US007351548B2

(12) United States Patent
Rambach

(10) Patent No.: US 7,351,548 B2
(45) Date of Patent: Apr. 1, 2008

(54) **CULTURE MEDIUM FOR DETECTING BACTERIA OF *LISTERIA* GENUS**

(76) Inventor: Alain Rambach, 73, Boulevard Montparnasse, 75006 Paris (FR)

( * ) Notice: Subject to any disclaimer, the term of this patent is extended or adjusted under 35 U.S.C. 154(b) by 163 days.

(21) Appl. No.: 10/250,483

(22) PCT Filed: Jan. 4, 2002

(86) PCT No.: PCT/FR02/00024

§ 371 (c)(1),
(2), (4) Date: Nov. 21, 2003

(87) PCT Pub. No.: WO02/053705

PCT Pub. Date: Jul. 11, 2002

(65) Prior Publication Data

US 2004/0072279 A1     Apr. 15, 2004

(30) Foreign Application Priority Data

Jan. 5, 2001   (FR)   ................... 01/00121

(51) Int. Cl.
*C12Q 1/04*  (2006.01)
(52) U.S. Cl. ...................................... 435/34
(58) Field of Classification Search .................... None
See application file for complete search history.

(56) References Cited

U.S. PATENT DOCUMENTS 5,164,301 A * 11/1992 Thompson et al. ........... 435/29
5,330,889 A    7/1994 Monget
5,962,251 A   10/1999 Rambach
6,228,606 B1 * 5/2001 Facon et al. ................. 435/29

OTHER PUBLICATIONS

K.G. Kerr et al., "Evaluation of the Rosco system for the identification of *Listeria* species", J. Med. Microbiol, 1991, pp. 193-196, vol. 35.
P. Carlson et al., "Evaluation of a Commercial Kit in the Identification of Arcanobacterium haemolyticum and Actinomyces pyogenes", Eur. J. Clin. Microbiol. Infect. Dis, 1994, pp. 507-509, vol. 13.
F. del Corral et al., "Evaluation of the API-ZYM system for identification of *Listeria*", Food Microbiology, 1990, pp. 99-106, vol. 7.
S.U. Walkley et al., "Bone marrow transplantation corrects the enzyme defect in storage disease", Proc. Natl. Acad. Sci. USA, Apr. 1994, pp. 2970-2974, vol. 91.

* cited by examiner

*Primary Examiner*—Robert B. Modesi
*Assistant Examiner*—Amanda P. Wood
(74) *Attorney, Agent, or Firm*—Blakely, Sokoloff, Taylor & Zafman LLP

(57) ABSTRACT

The invention concerns a culture medium for isolating bacteria of *Listeria* genus, in particular *L. monocytogenes*, characterized in that it comprises in a *Listeria* culture medium, at least a specific agent for identifying γ-mannosidase for use in solid medium.

6 Claims, No Drawings

CULTURE MEDIUM FOR DETECTING BACTERIA OF *LISTERIA* GENUS

The present invention relates to a chromogenic culture medium intended to demonstrate bacteria of the *Listeria* genus, in particular *Listeria monocytogenes*.

Both in the clinical field and in the agrofoods field, investigating *Listeria*, and in particular *Listeria monocytogenes*, is increasingly important, since these bacteria are often disseminated in agrofood products and lead to serious infections in sensitive patients (pregnant women, elderly individuals, etc.).

In fact, for a few years, governments have been setting up increasingly strict surveillance networks, in particular for products of the agrofoods industry. Thus, a generalization of the epidemiological surveillance of *Listeria monocytogenes* is observed.

It is therefore important to have a reliable and rapid test for detecting contaminations with these bacteria, which test must be both sensitive and specific.

There exist today certain culture media for detecting *Listeria*, such as PALCAM or OXFORD medium which are more or less selective, which make it possible to detect the presence of *Listeria* in samples. The results obtained using these media can exhibit certain inaccuracies implicating the need to carry out other tests to confirm the presence of *L. monocytogenes*.

These media are in fact based on a combination of antimicrobial agents providing selectivity and the detection of enzymes providing specificity. However, both the selectivity and the specificity of these media can be improved, since they bring about in particular the presence of many false positives or false negatives. A disadvantage of these media is that they do not make it possible to distinguish the species *L. monocytogenes*.

Media also exist which include a test based on the detection of phospholipases in order to directly detect *L. monocytogenes* by specific coloration of the colony or by a specific halo surrounding the colony. However, these tests are also positive for *L. ivanovii*, which is also phospholipase+in nature.

It was also suggested to differentiate *L. monocytogenes* from *L. ivanovii* in an identification step following the isolation step, using in particular a test based on a difference in an "aminopeptidase" phenotype.

For the purposes of differentiating *L. monocytogenes* from *L. ivanovii*, the present invention is based on the detection of alpha-mannosidase, a characteristic which is positive for *L. monocytogenes* and negative for *L. ivanovii*. This characteristic can, for example, be revealed on pure cultures using the enzyme substrate nitrophenyl-α-mannoside, which is colorless and which releases a yellow-colored nitrophenyl when the test is positive.

The present invention demonstrates that it is possible to reveal the α-mannosidase in colonies on solid medium by detecting the α-mannosidase with a chromogenic or fluorogenic substrate in the solid medium. The use of a substrate for α-mannosidase in a solid medium, derived for the first time in the present application, in particular has the advantage of preparing solid media in which it is possible to differentiate *L. monocytogenes* from *L. ivanovii* as soon as isolation has been carried out, without having to carry out further tests.

Thus, the present invention relates to a novel culture medium for detecting and/or discriminating bacteria of the *Listeria* genus, characterized in that it comprises, in a *Listeria* culture medium, at least one specific agent for identifying α-mannosidase which can be used in solid medium. Said specific agent for identifying α-mannosidase which can be used in solid medium is preferably a chromogenic or fluorogenic agent chosen from α-mannosidase substrates.

The chromogenic agent which is an α-mannosidase substrate preferably comprises a precipitatable chromophore which is released by hydrolysis of the substrate by its enzyme. Thus, the bacterial colony becomes colored as a function of the chromophore released, the chromophore released being solid in the culture medium, and therefore remaining localized at the colony where it was released.

Preferably, said chromophore is chosen from the indoxyl, haloindoxyl (bromoindoxyl, chloroindoxyl, fluoroindoxyl, iodoindoxyl, dichloroindoxyl, chlorobromoindoxyl, trichloroindoxyl), methylindoxyl or hydroxyquinoline derivatives. Preferred derivatives are in particular chosen from the following derivatives: 6-chloroindoxyl, 5-bromoindoxyl, 3-bromoindoxyl, 6-fluoroindoxyl, 5-iodoindoxyl, 4,6-dichloroindoxyl, 6,7-dichloroindoxyl, 5-bromo-4-chloroindoxyl, 5-bromo-6-chloroindoxyl, 4,6,7-trichloroindoxyl, N-methylindoxyl and 8-hydroxyquinoline.

When said α-mannosidase substrate is coupled to a fluorophore, 4-methylumbelliferyl is preferably used.

Preferably, the α-mannosidase substrate is indoxyl-α-mannoside. The concentration of the chromogenic agent in the medium is between approximately 0.01 and 0.5 g/l. A preferred concentration is 0.05 g/l.

It may also be advantageous to add a colored-reaction activator, to the medium, in order to improve the quality of the reaction observed. A suitable activator for such a use is methyl-α-mannoside, which is integrated into the medium at a concentration of between approximately 0.01 and 0.5 g/l, preferably 0.25 g/l.

The medium according to the present invention thus makes it possible to detect *L. monocytogenes*, and to discriminate this bacterium with respect to *L. ivanovii*, without carrying out any additional test. In order to optimize the results given by the medium according to the invention, it may be advantageous to add factors selective for *Listeria*, as used in the media of the prior art. A medium specific for *L. monocytogenes* is therefore obtained.

A subject of the invention is also the use of a culture medium according to the invention, for detecting and/or discriminating bacteria of the *Listeria* genus, in particular *L. monocytogenes*.

A subject of the present invention is also a method for detecting and/or discriminating bacteria of the *Listeria* genus, in a sample, characterized in that it comprises the following steps:

a. inoculating a culture medium according to the invention with said sample or an inoculum derived from the sample, b. detecting the presence of bacteria of the *Listeria* genus on said culture medium, c. optionally, differentiating *L. monocytogenes* from *L. ivanovii* and from the other *Listeria* present on said culture medium.

EXAMPLES

Example 1

A preferred medium for implementing the invention comprises (per liter):

| | |
|---|---|
| agar | 10 g |
| calf brain infusion | 12.5 g |
| proteose peptone | 10 g |
| beef heart infusion | 5 g |
| sodium chloride | 5 g |
| $Na_2HPO_4$ | 4 g |
| $KH_2PO_4$ | 2 g |
| glucose | 2 g |
| lithium chloride | 7.5 g |
| lecithin | 3 g |
| ofloxacin | 0.0004 g |
| colistin | 0.015 g |
| ceftazidime | 0.0134 g |
| methyl-α-mannoside | 0.25 g |
| indoxyl-α-mannoside | 0.05 g |

Example 2

The plating out of bacteria on the medium according to the invention gave the following results (incubation for 24 hours at 37° C.).

| | Halo | Colony center |
|---|---|---|
| *L. monocytogenes* | white | blue |
| *L. ivanovii* | white | colorless |
| other Listeria | no halo | — |

The use of the medium according to the invention therefore makes it possible to detect and discriminate *L. monocytogenes*, *L. ivanovii* and the other species of *Listeria*.

The invention claimed is:

1. A culture medium for detecting *Listeria monocytogenes* (*L. monocytogenes*) and for discriminating it from *Listeria ivanovii* (*L. ivanovii*) and for discriminating both *L. monocytogenes* and *L. ivanovii* from other *Listeria* bacteria, comprising, in a solid *Listeria* culture medium, at least one chromogenic agent wherein the chromogenic agent is an α-mannosidase substrate capable of releasing a precipitable chromophore and further comprising methyl-α-mannoside.

2. The culture medium of claim 1, wherein the precipitable chromophore is one of 8-hydroxyquinoline, indoxyl, N-methylindoxyl, or a haloindoxyl selected from the group consisting of bromoindoxyl, chloroindoxyl, fluoroindoxyl, iodoindoxyl, dichloroindoxyl, chlorobromoindoxyl, trichloroindoxyl, 6-chloroindoxyl, 5-bromoindoxyl, 3-bromoindoxyl, 6-fluoroindoxyl, 5-iodoindoxyl, 4,6-dichloroindoxyl, 6,7-dichloroindoxyl, 5-bromo-4-chloroindoxyl, 5-bromo-6-chloroindoxyl, and 4,6,7-trichloroindoxyl.

3. The culture medium of claim 1, further comprising factors selective for *Listeria*.

4. The culture medium of claim 1, wherein the α-mannosidase substrate is indoxyl-α-mannoside.

5. The culture of claim 1, which comprises (per liter):

| | |
|---|---|
| agar | 10 g |
| calf brain infusion | 12.5 g |
| proteose peptone | 10 g |
| beef heart infusion | 5 g |
| sodium chloride | 5 g |
| Na2HPO4 | 4 g |
| KH2PO4 | 2 g |
| glucose | 2 g |
| lithium chloride | 7.5 g |
| lecithin | 3 g |
| ofloxacin | 0.0004 g |
| colistin | 0.0134 g |
| methyl-α-mannoside | 0.25 g |
| indoxyl-α-mannoside | 0.05 g. |

6. A method for detecting *L. monocyto genes* and for discriminating it from *L. ivanovii* in a sample, and for discriminating both *L. monocyto genes* and *L. ivanovii* from other *Listeria* bacteria in a sample comprising:

a. inoculating a culture medium as defined in claim 1, with said sample or an inoculum derived from said the sample, b. detecting the presence of bacteria of the *Listeria* genus on the culture medium, c. differentiating *L. monocyto genes* from *L. ivanovii* and both *L. monocytogenes* and *L. ivanovii* from other *Listeria* that may be present on the culture medium.

* * * * *